United States Patent [19]

Kawata

[11] Patent Number: 5,326,876
[45] Date of Patent: Jul. 5, 1994

[54] PROCESS FOR PREPARING AN ALKYL SULFONATE DERIVATIVE

[75] Inventor: Ken Kawata, Minami-ashigara, Japan

[73] Assignee: Fuji Photo Film Co., Ltd., Kanagawa, Japan

[21] Appl. No.: 31,135

[22] Filed: Mar. 12, 1993

Related U.S. Application Data

[63] Continuation-in-part of Ser. No. 904,511, Jun. 25, 1992, abandoned.

[30] Foreign Application Priority Data

Jun. 26, 1991 [JP] Japan .................................. 3-181978

[51] Int. Cl.$^5$ .................. C07D 293/10; C07D 277/60; C07D 263/58; C07D 209/56
[52] U.S. Cl. .................................. 548/100; 548/150; 548/217; 548/221; 548/302.1; 548/427; 548/450
[58] Field of Search .............. 548/100, 150, 217, 221, 548/302.1, 427, 450

[56] References Cited

U.S. PATENT DOCUMENTS

| | | | |
|---|---|---|---|
| 3,776,739 | 12/1973 | Sato et al. | 548/150 |
| 3,943,142 | 3/1976 | Owen | 548/150 |
| 4,028,353 | 6/1977 | Barror | 548/150 |
| 4,308,390 | 12/1981 | Kempfer et al. | 548/150 |
| 4,469,785 | 9/1984 | Tanaka et al. | 548/150 |
| 4,883,880 | 11/1989 | Kempfer et al. | 549/40 |

OTHER PUBLICATIONS

CA113(25):231386y Method for . . . dyes, Bach et al., p. 725, 1990.

CA113(3):23888m Preparation of . . . dyes, Kampfer et al., p. 660, 1990.

Primary Examiner—Mary C. Lee
Assistant Examiner—Joseph K. McKane
Attorney, Agent, or Firm—Sughrue, Mion, Zinn, Macpeak & Seas

[57] ABSTRACT

A process for preparing an alkyl sulfonate derivative comprises causing a nitrogen-containing heterocyclic compound represented by the following formula (1):

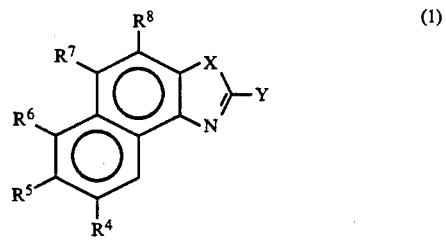

wherein X represents —O—, —S—, —NR$^1$—, —Se—, —Te— or —CR$^2$R$^3$—, in which each of R$^1$, R$^2$ and R$^3$ independently represents a hydrogen atom or a lower alkyl group, Y represents a hydrogen atom, a mercapto group, an arylthio group, an aralkyl group, a sulfo group, a halogen atom, an alkyl group, an alkylthio group, an alkylsulfonyloxy group or an arylsulfonyloxy group and each of R$^4$, R$^5$, R$^6$, R$^7$ and R$^8$ represents a hydrogen atom, an alkyl group, an aryl group, an alkoxy group which may be substituted with a sulfo group, an aryloxy group, an alkylthio group, a haloalkyl group, a halogen atom, a cyano group, a carboxy group or a sulfo group, otherwise R$^4$ and R$^5$, R$^6$ and R$^6$, R$^6$ and R$^7$ and R$^7$ and R$^8$ are, in at least one of these combinations, bonded each other to form an aromatic ring or a cycloalkene ring; to react in the presence of Lewis acid with an aliphatic sultone to give an alkyl sulfonate derivative corresponding to the above formula (1).

12 Claims, No Drawings

PROCESS FOR PREPARING AN ALKYL SULFONATE DERIVATIVE

This is a continuation-in-part of application Ser. No. 07/904,511 filed Jun. 25, 1992, abandoned.

FIELD OF THE INVENTION

The present invention relates to a novel process for preparing an alkyl sulfonate derivative having a heterocyclic ring.

BACKGROUND OF THE INVENTION

It is already known that a cyanine dye of which the side chain of a mother nucleus (a heterocyclic ring directly bonded to a polymethine chain) is a sulfoalkyl group is used for a photographic material. The sulfoalkyl group is generally bonded to the quaternary nitrogen of a nitrogen-containing heterocyclic ring which constitutes the mother nucleus of the cyanine dye.

The above cyanine dye having the sulfoalkyl group directly bonded to the quaternary nitrogen is generally produced from a precursor, i.e., an alkyl sulfonate derivative having a heterocyclic ring, which has the following formula (5) or (7):

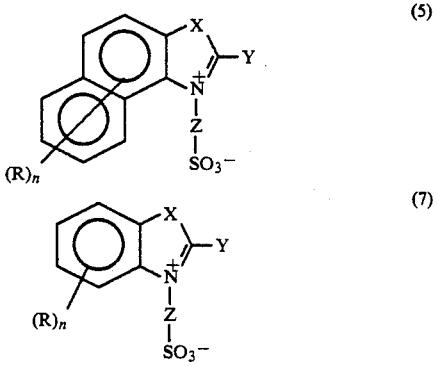

wherein X represents —O—, —S—, —NR$^1$—, —Se—, —Te— or —CR$^2$R$^3$— (in which each of R$^1$, R$^2$ and R$^3$ independently represents a hydrogen atom or a lower alkyl group which may have a substituent and R$^2$ and R$^3$ may form a ring by bonding each other), Y represents a hydrogen atom, mercapto group, an alkylthio group which may have a substituent and an alkyl group, n represents an integer of 0 to 6, and R represents a substituent, the substituents being the same or different from each other in the case of n of not less than 2. The cyanine dye obtained by the compound represented by the formula (5) or (7) is described in Japanese Patent Provisional Publications No. 1-187543 and No. 3-105339.

For example, an alkyl sulfonate derivative containing a nitrogen-atom can be prepared by causing a nitrogen containing compound (e.g., amine) to react with a chain alkyl sulfonate (salt) activated by introducing a halogen atom or sulfonyloxy group to bond the sulfoalkyl group to the nitrogen.

This method is considered to be applied to the preparation of the alkyl sulfonate derivative having a nitrogen-containing heterocyclic ring represented by the above formula (5) or (7). In more detail, it would be considered that a nitrogen-containing heterocyclic compound having the following formula (4) or (6):

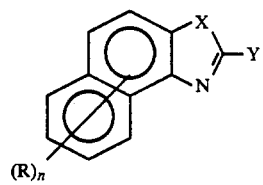

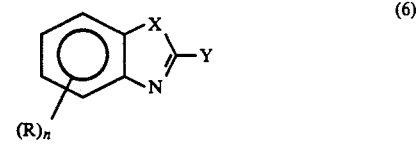

wherein Y, X, R, n and Z represent the meanings defined above; is caused to react with a chain alkyl sulfonate (salt) activated above to bond the sulfoalkyl group to the nitrogen, whereby the alkyl sulfonate derivative presented by the above formula (5) or (7) is obtained.

The activated alkyl sulfonate serves advantageously as a sulfoalkylated agent for a compound to be sulfoalkylated, in the case that the compound has a high nucleophilicity so that its sulfoalkylated reaction proceeds under relatively mild conditions. However, in the case that the nitrogen-containing heterocyclic compound of the above formula (4), which has not a benzene ring but a naphthalene ring, is caused to react with the activated chain alkyl sulfonate (salt), the reaction needs more heating due to its low reactivity so that the activated portion of the alkyl sulfonate is apt to eliminate. Hence, the alkyl sulfonate derivative represented by the above formula (5) can not be obtained using the alkylsulfonate.

Otherwise, as an sulfoalkylated agent having an activated hydrogen, an aliphatic sultone is already known. It is described in Japanese Patent Provisional Publication No. 1-187543 that the aliphatic sultone reacts with a nitrogen-containing heterocyclic compound such as a compound having the above formula (6) to introduce a sulfoalkyl group into the heterocyclic compound, whereby the alkyl sulfonate derivative of the above formula (5) is obtained. Generally, introduction of the sulfoalkyl group into the nitrogen-containing heterocyclic compound of the above formula (4) having a naphthalene ring is also conducted in the same manner as above. Thus, in the case that the sultone is caused to react with the nitrogen-containing heterocyclic compound of the above formula (4) or (6) to bond the nitrogen of the heterocyclic compound, the alkyl sulfonate derivative of the above formula (5) or (7) would be obtained. Because the elimination occurring in use of the activated chain alkyl sulfonate hardly occurs in the case of use of the sultone.

However, the study of the present inventor has revealed that the reaction of the sultone with the nitrogen-containing heterocyclic compound of the above formula (4) gives the derivative in an extremely low yield. The reason is deemed as follows:

A steric hindrance derived from a hydrogen atom or substituent which is bonded to 8.position carbon atom (on naphthalene ring) of the nitrogen-containing heterocyclic compound of the above formula (4), inhibits the sultone molecule from approach to the nitrogen atom of the nitrogen-containing heterocyclic compound.

SUMMARY OF THE INVENTION

It is an object of the present invention to provide for a novel process for preparing an alkyl sulfonate derivative having a nitrogen-containing heterocyclic ring represented by the following formula (3) in a high yield.

There is provided by the present invention a process for preparing an alkyl sulfonate derivative comprising:

causing a nitrogen containing heterocyclic compound represented by the following formula (1):

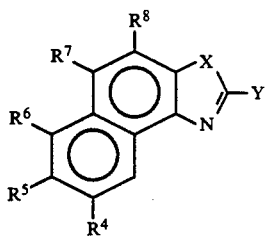
(1)

X represents —O—, —S—, —NR$^1$—, —Se—, —Te— or —CR$^2$R$^3$—, in which each of R$^1$, R$^2$ and R$^3$ independently represents a hydrogen atom or a lower alkyl group which may be substituted with a halogen atom, a lower alkoxy group, an amino group or a hydroxy group and R$^2$ and R$^3$ may be bonded each other to form a 5 to 8-membered ring containing oxygen or nitrogen together with a carbon atom of a pyrrole ring to which R$^2$ and R$^3$ are bonded, Y represents a hydrogen atom, a mercapto group, an arylthio group which may be substituted with a halogen atom, an aralkyl group which may be substituted with a halogen atom, a sulfo group, a halogen atom, an alkyl group which may be substituted with a halogen atom, an alkylthio group which may be substituted with a sulfo group, an alkoxy group or an alkoxyalkoxy group, an alkylsulfonyloxy group which may be substituted with a halogen atom or an arylsulfonyloxy group which may be substituted with a halogen atom or an alkyl group and each of R$^4$, R$^5$, R$^6$, R$^7$ and R$^8$ independently represents a hydrogen atom, an alkyl group, an aryl group, an alkoxy group which may be substituted with a sulfo group, an aryloxy group, an alkylthio group, a haloalkyl group, a halogen atom, a cyano group, a carboxy group or a sulfo group;

to react in the presence of Lewis acid with an aliphatic sultone represented by the following formula (2):

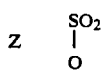
(2)

wherein Z represents an alkylene group which may substituted with an alkyl group, an alkoxy group or halogen atom;

to give an alkyl sulfonate derivative represented by the following formula (3):

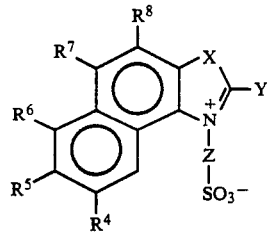
(3)

wherein Y, R$^4$, R$^5$, R$^6$, R$^7$, R$^8$, X and Z represent the meanings defined above.

Further, there is provided by the invention a process for preparing an alkyl sulfonate derivative comprising:

causing a nitrogen-containing heterocyclic compound represented by the above formula (1): wherein X represents —O—, —S—, —NR$^1$—, —Se—, —Te— or —CR$^2$R$^3$—, in which each of R$^1$, R$^2$ and R$^3$ independently represents a hydrogen atom or a lower alkyl group which may be substituted with a halogen atom, a lower alkoxy group, an amino group or a hydroxy group and R$^2$ and R$^3$ may be bonded each other to form a 5 to 8-membered ring containing oxygen or nitrogen together with a carbon atom of a pyrrole ring to which R$^2$ and R$^3$ bond, Y represents a hydrogen atom, a mercapto group, an arylthio group which may be substituted with a halogen atom, an aralkyl group which may be substituted with a halogen atom, a sulfo group, a halogen atom, an alkyl group which may be substituted with a halogen atom, an alkylthio group which may be substituted with a sulfo group, an alkoxy group or an alkoxyalkoxy group, an alkylsulfonyloxy group which may be substituted with a halogen atom or an arylsulfonyloxy group which may be substituted with a halogen atom or an alkyl group, R$^4$ and R$^5$, R$^5$ and R$^6$, R$^6$ and R$^7$ and R$^7$ and R$^8$ are, in at least one of the combinations, bonded each other to form an aromatic ring or a cycloalkene ring together with a divalent hydrocarbon group of a naphthalene ring to which R$^4$, R$^5$, R$^6$, R$^7$ and R$^8$ are bonded, and R$^4$, R$^5$, R$^6$, R$^7$ and R$^8$ which do not participate the formation of the ring represent a hydrogen atom, an alkyl group, an aryl group, an alkoxy group which may be substituted with a sulfo group, an aryloxy group, an alkylthio group, a haloalkyl group, a halogen atom, a cyano group, a carboxy group or a sulfo group;

to react in the presence of Lewis acid with an aliphatic sultone represented by the above formula (2): wherein Z represents an alkylene group which may substituted with an alkyl group, an alkoxy group or halogen atom;

to give an alkyl sulfonate derivative represented by the above formula (3): wherein Y, R$^4$, R$^5$, R$^6$, R$^7$, R$^8$, X and Z represent the meanings defined above.

The present invention enables the preparation of an alkyl sulfonate derivative having a nitrogen-containing heterocyclic ring represented by the above formula (3) in a high yield from a nitrogen-containing heterocyclic compound represented by the above formula (1) and an aliphatic sultone. The alkyl sulfonate derivative having a nitrogen-containing heterocyclic ring is a necessary material for the preparation of a cyanine dye of which the side chain of a mother nucleus is a sulfoalkyl group.

DETAILED DESCRIPTION OF THE INVENTION

The process for the preparation of an alkyl sulfonate derivative according to the present invention comprises the step of causing a nitrogen-containing heterocyclic compound represented by the above formula (1) to react in the presence of Lewis acid with an aliphatic sultone having the above formula (2) to give an alkyl sulfonate derivative represented by the above formula (3) corresponding to the above nitrogen-containing heterocyclic compound.

The nitrogen-containing heterocyclic compounds, which is one of materials of the invention, is a compound having a ring fused with a naphthalene ring of the formula (1) or a compound having no ring fused with the naphthalene ring.

First, the nitrogen-containing heterocyclic compound having no condensed ring is described below.

X represents —O—, —S—, —NR$^1$—, —Se—, —Te— or —CR$^2$R$^3$—, each of R$^1$, R$^2$ and R$^3$ independently represents a hydrogen atom or a lower alkyl group which may be substituted with a halogen atom, a lower alkoxy group or a hydroxy group, and R$^2$ and R$^3$ may be bonded each other to form a 5 to 8-membered ring containing oxygen or nitrogen together with a carbon atom of a pyrrole ring to which R$^2$ and R$^3$ are bonded. X generally is —O—, —S—, —Se—, —NR$^1$— or —CR$^2$R$^3$—, X is preferred to be —O—, —S— or —Se—and particularly preferred to be —S—. R$^1$, R$^2$ and R$^3$ are preferred to be a hydrogen atom or an alkyl group having 1 4 carbon atoms such as methyl, ethyl, propyl or butyl, and particularly preferred to be a hydrogen atom, methyl group or ethyl group. A substituent which R$^1$, R$^2$ and R$^3$ may have is a halogen atom (e.g., chlorine atom), an alkoxy group having 1 to 4 carbon atoms, an amino group (e.g., methylamino) or a hydroxy group. The 5 to 8-membered ring formed by R$^2$ and R$^3$ is preferred to be a 5 or 6-membered hydrocarbon ring containing oxygen or nitrogen and more prefered to be 6-membered hydrocarbon ring containing oxygen or nitrogen such as pentamethyleneoxide ring or a N-methyl-piperazine ring.

Y represents a hydrogen atom, a mercapto group, an arylthio group which may be substituted with a halogen atom, an aralkyl group which may be substituted with a halogen atom, a sulfo group (sulfo or sulfonate), a halogen atom, an alkyl group which may be substituted with a halogen atom, an alkylthio group which may be substituted with a sulfo group, an alkoxy group or an alkoxyalkoxy group, an alkylsulfonyloxy group which may be substituted with a halogen atom, or an arylsulfonyloxy group which may be substituted with a halogen atom or an alkyl group. Y generally represents a hydrogen atom, a mercapto group, an arylthio group, an aralkyl group, a sulfo group, an alkyl group which may be substituted with a halogen atom, an alkylthio group which may be substituted with a sulfo group. Y is preferred to be an alkyl group having 1 to 5 carbon atoms (e.g., methyl and ethyl), an alkylthio group having 1 to 4 carbon atoms, a phenylthio group or a benzyl group and particularly preferred to be methyl.

Each of R$^4$, R$^5$, R$^6$, R$^7$ and R$^8$ represents a hydrogen atom, an alkyl group, an aryl group, an alkoxy group which may be substituted with a sulfo group (sulfo or sulfonate), an aryloxy group, an alkylthio group, a haloalkyl group, a halogen atom, a cyano group, a carboxy group or a sulfo group. Each of R$^4$, R$^5$, R$^6$, R$^7$ and R$^8$ is preferred to be a hydrogen atom, an alkyl group having 1 to 3 carbon atoms, an aryl group having 6 to 14 carbon atoms (e.g., phenyl, naphthyl, anthryl or phenanthryl), an alkoxy group having 1 to 25 carbon atoms which may be substituted with a sulfo group, an aryloxy group (e.g., phenoxy), a haloalkyl group having 1 to 3 carbon atoms, an alkylthio group having 1 to carbon atoms, a halogen atom, a cyano group, a carboxy group or a sulfo group. Each of R$^4$, R$^5$, R$^6$, R$^7$ and R$^8$ is particularly preferred to be a hydrogen atom, an alkyl group having 1 to 3 carbon atoms, a phenoxy group, an alkoxy group having 1 to 25 carbon atoms which may be substituted with a sulfo group, an alkylthio group having 1 to 3 carbon atoms, a halogen atom or a sulfo group. Further, one or two of R$^4$, R$^5$, R$^6$, R$^7$ and R$^8$ is preferred to represent the above substituent except a hydrogen atom.

Otherwise, another nitrogen-containing heterocyclic compound according to the invention has a ring fused with a naphthalene ring to which R$^4$, R$^5$, R$^6$, R$^7$ and R$^8$ are bonded and is different in structure from the above compound although is represented by the above formula (1). In more detail, R$^4$ and R$^5$, R$^5$ and R$^6$, R$^6$ and R$^7$, and R$^7$ and R$^8$ are, in at least one of these combinations, bonded each other to form an aromatic ring or a cycloalkene ring together with a divalent hydrocarbon group of a naphthalene ring to which R$^4$, R$^5$, R$^6$, R$^7$ and R$^8$ are bonded. Examples of the aromatic ring preferably includes a benzene ring, a naphthalene ring, a anthracene ring and a phenanthrene ring, and more preferably a benzene ring. Examples of the cycloalkene ring preferably include a cyclohexene ring and a cyclopentene, and more preferably a cyclohexene ring. Further, R$^4$, R$^5$, R$^6$, R$^7$ and R$^8$ which do not participate in the formation of the ring, preferably represent a hydrogen atom, and however may represent the above substituents (i.e., a hydrogen atom, an alkyl group, an aryl group, an alkoxy group which may be substituted with a sulfo group, an aryloxy group, a haloalkyl group, an alkylthio group, a halogen atom, a cyano group, a carboxy group or a sulfo group).

The ring is preferably formed by one or two of combinations consisting of R$^4$ and R$^5$, R$^5$ and R$^6$, R$^6$ and R$^7$, and R$^7$ and R$^8$, and more preferably formed by one of these combinations. In more detail, the naphthalene ring preferably has one or two rings mentioned above, and more preferably has one ring. Among combinations of R$^4$ and R$^5$, R$^5$ and R$^6$, R$^6$ and R$^7$, and R$^7$ and R$^8$ to form the ring, the preferred combination to form the aromatic ring is R$^4$ and R$^5$, or R$^5$ and R$^6$, and more preferred combination is R$^5$ and R$^6$. The preferred combination to form the cycloalkene ring is R$^6$ and R$^7$.

The alkylsulfonate derivative represented by the above formula (3) is conventionally used in an intermediate of a cyanine dye employable for a photographic material as mentioned previously. Therefore, the nitrogen-containing heterocyclic compound represented by the above formula (1) may be selected corresponding to the structure of the alkylsulfonate derivative (the formula (3)) required as the intermediate.

Preferred examples of the nitrogen-containing hetero cyclic compound represented by the above formula (1) are as follows:

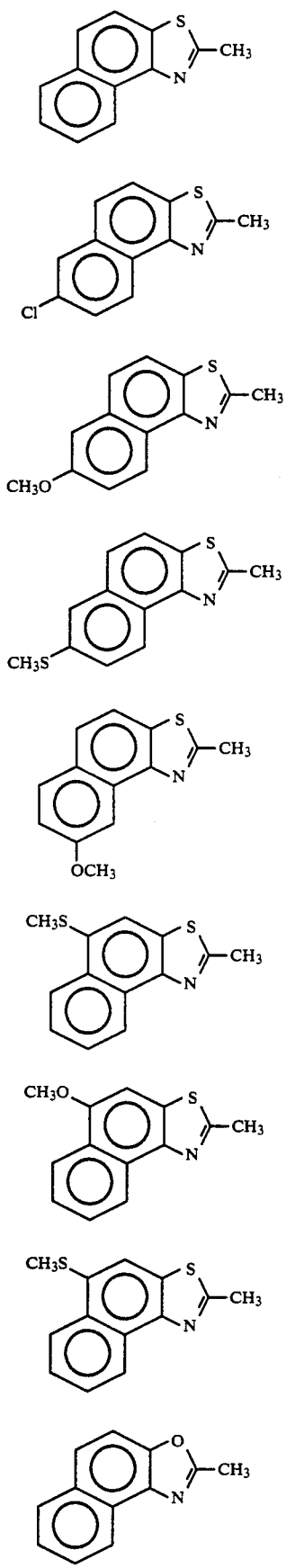
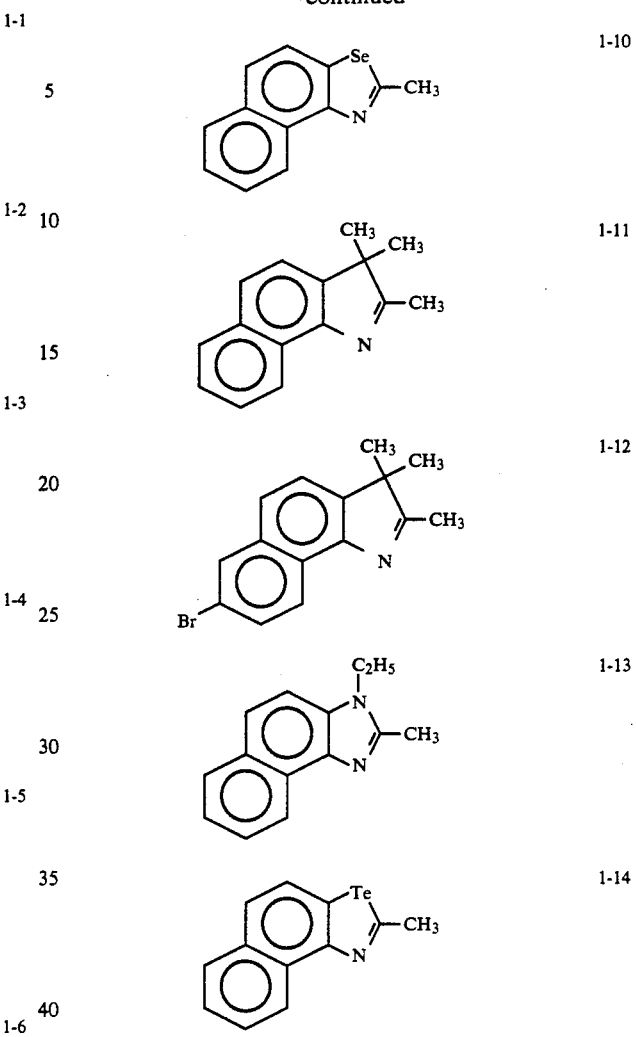

The aliphatic sultone, which is other material according to the invention, is represented by the above formula (2). In the formula 2), Z represents an alkylene group which may have a substituent. Z is preferred to be a linear alkylene group (e.g., propylene group or butylene group) having 3-4 carbon atoms which has not substituent, or the linear alkylene group which has a substituent selected from an alkyl group having 1-6 carbon atoms and halogen atom. Further, Z is particularly preferred to be a linear alkylene group (e.g., propylene group or butylene group) having 3-4 carbon atoms which has no substituent, or the linear alkylene group which has a substituent selected from an alkyl group (e.g., methyl group, ethyl group, propyl group or butyl group) having 1-4 carbon atoms, an alkoxy group (e.g., methoxy group, ethoxy group or propoxy group) having 1-3 carbon atoms and halogen atom (e.g., fluorine or chlorine). Preferred examples of the aliphatic sultone include 1-3-propanesultone, 1-methyl-1,3-propanesultone, 1,4-butanesultone and 2-methyl-1,4-butanesultone.

In the invention, the reaction of the nitrogen-containing heterocyclic compound of the formula (1) with the aliphatic sultone of the formula (2) is conducted in the presence of Lewis acid. The Lewis acid employable for the invention may be any known Lewis acid. From the viewpoints of a high yield of the alkylsulfonate derivative and easy after-treatment of the resultant reaction mixture, the Lewis acid is preferred to be a boron trifluoride etherate (complex), zinc chloride, aluminium chloride, stannic chloride or ferric chloride, and particularly preferred to be boron trifluoride etherate (e.g., boron trifluoride ethyl etherate).

Preferred examples of the alkylsulfonate compound represented by the above formula (3) which is obtained by the above process of the invention are as follows:

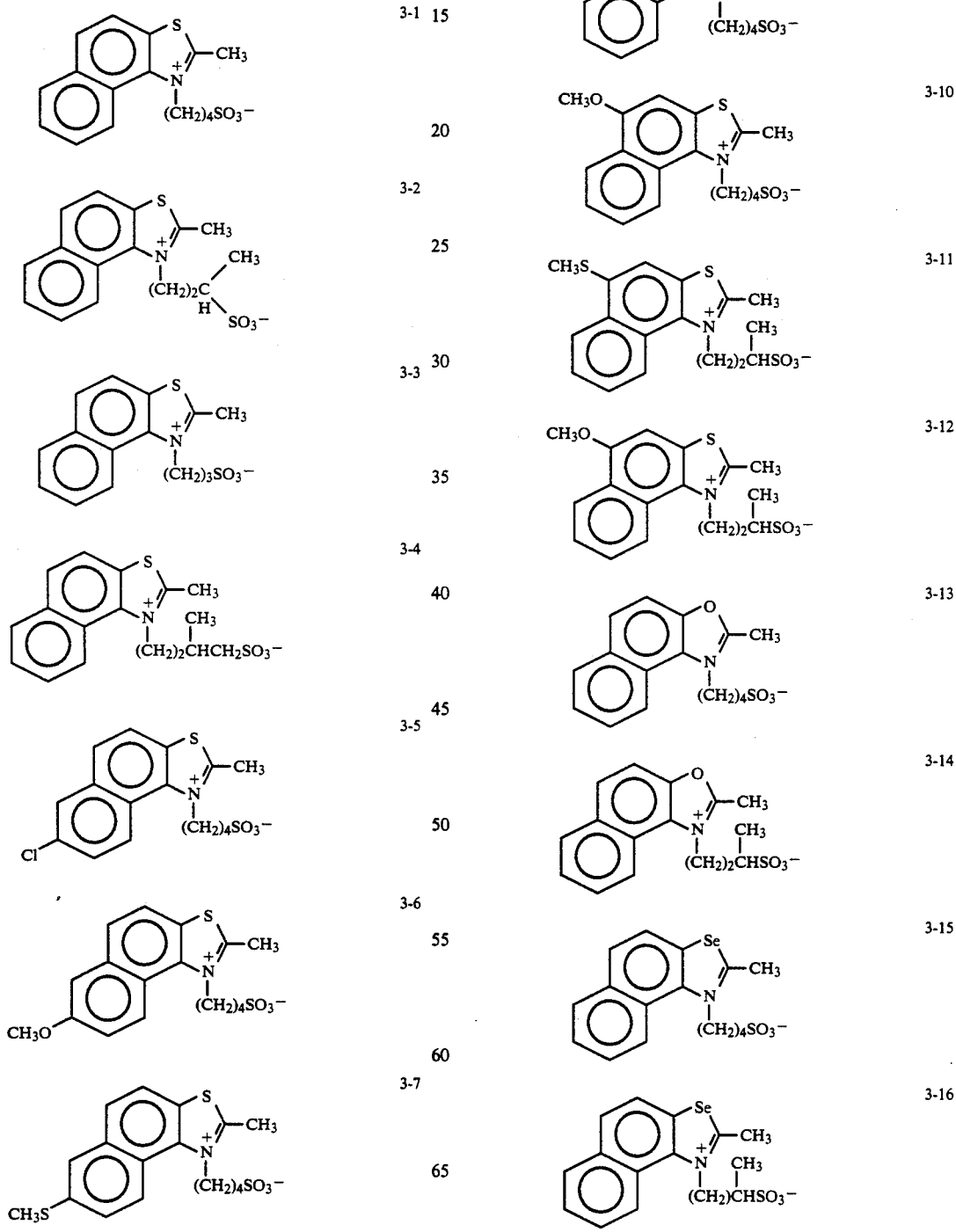

-continued 3-17

3-18

3-19

3-20

3-21

3-22

3-23

3-24

-continued 3-25

3-26

3-27

3-28

3-29

3-30

3-31

3-32

-continued 3-33

3-34

3-35

3-36

3-37

3-38

3-39

3-40

3-41

3-42

3-43

3-44

3-45

3-46

3-47

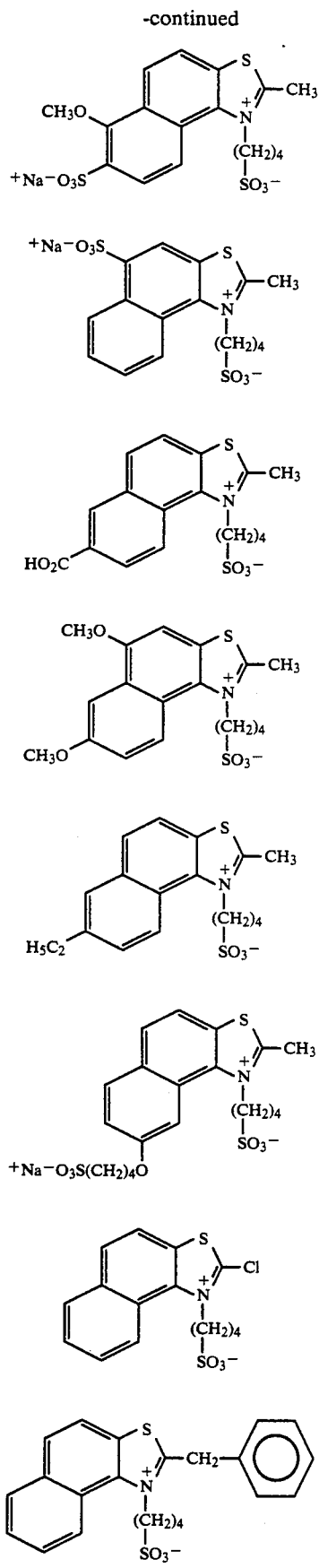
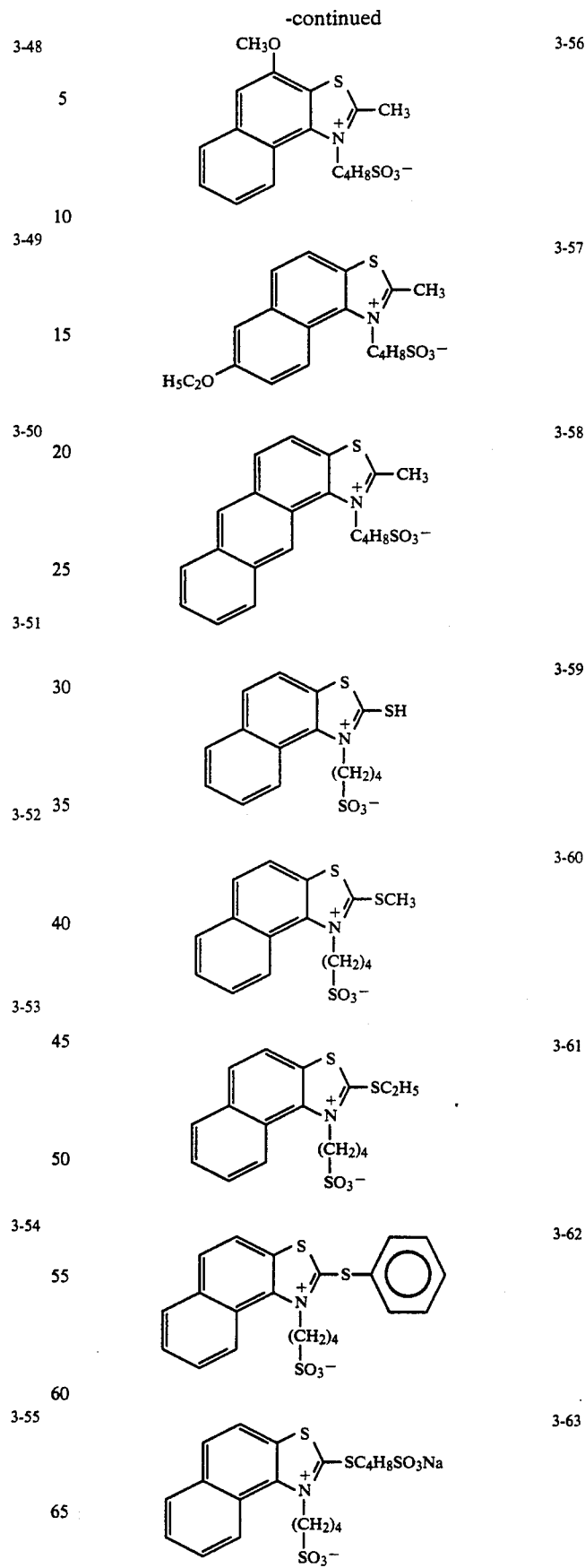

-continued 3-64
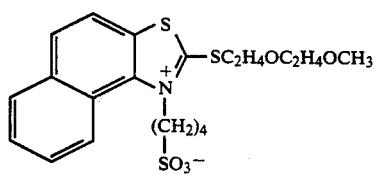

3-65
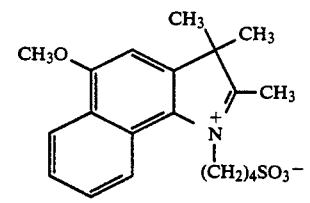

3-66
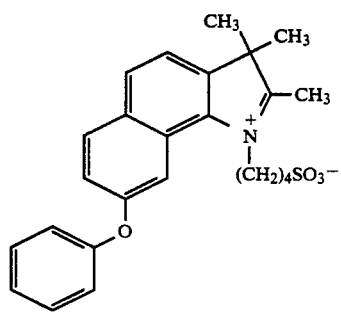

3-67
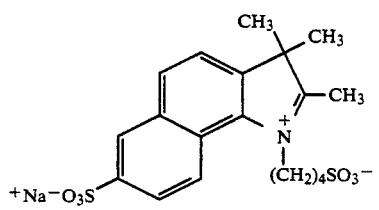

3-68
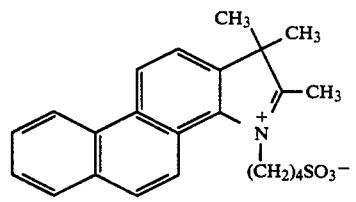

3-69
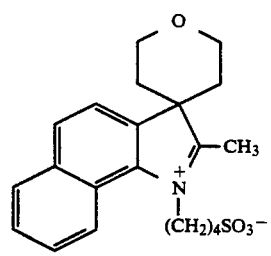

3-70
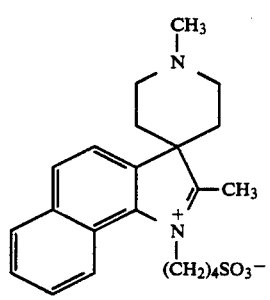

-continued 3-71
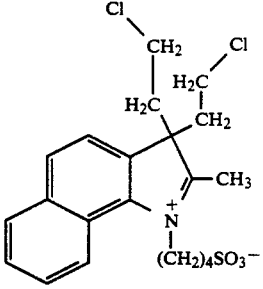

3-72
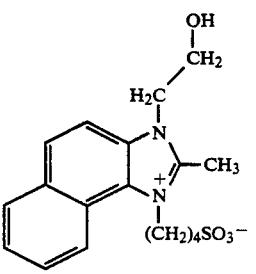

3-73
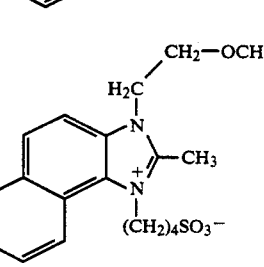

3-74
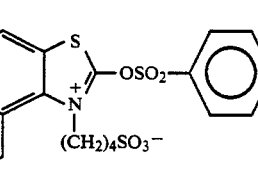

3-75
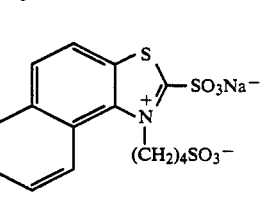

3-76
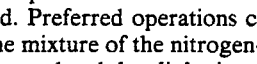

The process for preparing the alkyl sulfonate derivatives having the above formula (3) is conducted by heating the mixture of the nitrogen-containing heterocyclic compound of the formula (1), the aliphatic sultone of the formula (2) and Lewis acid at a desired temperature. Operations for conducting the process are not restricted. Preferred operations comprise the steps of heating the mixture of the nitrogen-containing heterocyclic compound and the aliphatic sultone, and adding gradually the Lewis acid to the mixture under stirring.

In the invention, the ratio between the nitrogen-containing heterocyclic compound and the aliphatic sultone {(the heterocyclic compound):(the sultone)} preferably is 1:1 to 1:5 by mole, and more preferably 1:1.5 to 1:2. The ratio between the nitrogen-containing heterocyclic compound and the Lewis acid {(the heterocyclic compound):(the Lewis acid)} preferably is 1:1 to 1:3 by mole, and more preferably 1:1 to 1:1.5, although the amount of the Lewis acid used is variable depending on the kinds of the nitrogen-containing heterocyclic compound, the aliphatic sultone and the Lewis acid.

In the invention, the temperature (reaction temperature) for heating the above mixture is preferably in the range of 120° C. to 250° C., and more preferably in the range of 160° C. to 190° C. In the case that the reaction temperature is lower than the lower limit of the above range, the yield of the resultant alkylsulfonate derivative decreases. In the case that the reaction temperature is higher than the upper limit of the above range, the yield of the resultant alkylsulfonate derivative hardly increases and the derivative and the materials come to be apt to decompose. Therefore, such heating brings about loss of heat energy.

It may be not required to use inert solvents in the reaction. If necessary, inert solvents (e.g., sulfolane) which have no participation in the reaction may be added into the reaction mixture.

Pressure inside a vessel into which the reaction mixture is introduced is preferred to be in such a range as the reaction mixture is kept in liquid state at the above temperature range. The yield of the reaction generally reaches the about maximum in the range of 10 minutes to 3 hours, although it is different depending on the materials used in the reaction or the reaction temperature.

In the reaction, the aliphatic sultone does not react with the nitrogen-containing heterocyclic compound but occasionally produces an acid. In this case, it is preferred to add into the reaction mixture a basic substance (e.g., sodium acetate or 2,6-litidine) which does not react with the resultant alkylsulfonate derivative.

After the reaction is complete, the alkylsulfonate derivative is separated from the obtained reaction mixture according to a known method and the derivative is further purified if necessary. The methods to separate or purify the alkylsulfonate derivative may adopt the methods comprising the steps of pouring the reaction mixture into a poor solvent such as ethyl acetate to allow the alkylsulfonate derivative to crystallize, separating it by filtration, and recrystallizing it using alcohol solvent such as methanol, ethanol or propanol.

According to the above process of the invention, the yield of the alkylsulfonate derivative is not less than 40 weight % (generally not less than 50 weight %) based on the above nitrogen-containing heterocyclic compound.

The present invention is further described by the following examples.

EXAMPLE 1

Synthesis of 2-methylnaphtho[1,2-d]thiazorium 3-butanesulfonate (a compound number 3 1 of the formula (3) above)

In a round bottom flask provided with a stirrer and a reflux condenser were placed 14 g (0.07 mole) of 2-methylnaphtho[1,2-d]thiazole and 14 g (0.10 mole) of 1,4-butane sultone, and they (the contents inside the flask) were heated at 160° C. by dipping the flask in an oil bath. With stirring the contents, 14 ml (0,11 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 12.0 g of white crystals were obtained and the yield of the crystals (as the subject compound) was 51%.

It was confirmed that the compound of the above white crystals was the same as the subject compound by NMR and FAB mass spectrum as set forth below.

[NMR]
δ:2.15 (q, 2H). 2.40 (m, 2H); 2.95 (t, 2H); 3.30 (s, 3H); 5.70 (t, 2H); 7.80–8.90 (m, 6H)

[FAB mass spectrum] m/e: 336

COMPARISON EXAMPLE 1

The procedure of Example 1 was repeated except for using no boron trifluoride ethyl etherate and changing the reaction temperature to 220° C. and the reaction time to 6 hours. However, 2.methylnaphtho[1,2-d]thiazorium 3-butane-sulfonate, which is an intended compound, was obtained in trace amount.

EXAMPLE 2

Synthesis of 2-methyl-6-methoxynaphtho[1,2-d]thiazorium 3-butanesulfonate (a compound number 3-6 of the formula (3) above).

In a round bottom flask provided with a stirrer and a reflux condenser were placed 16 g (0.07 mole) of 2-methyl-6-methoxynaphtho[1,2-d]thiazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 60° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 14.2 g of white crystals were obtained and the yield of the crystals (as the subject compound) was 6.2 %.

EXAMPLE 3

Synthesis of 2-methylnaphtho[1,2-d]oxazorium 3-butanesulfonate (a compound number 3.13 of the formula (3) above)

In a round bottom flask provided with a stirrer and a reflux condenser were placed 12.8 g (0.07 mole) of 2-methylnaphtho[1,2-d]oxazole and 14 g (0.10 mole) of 1,4-butanesultone, and they were heated at 160° C. by dipping the flask in an oil bath. With stirring the contents, 14 ml (0,11 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 15.6 g of white crystals were obtained and the yield of the crystals (as the subject compound) was 70%.

COMPARISON EXAMPLE 2

The procedure of Example 3 was repeated except for using no boron trifluoride ethyl etherate and changing the reaction temperature to 220° C. and the reaction time to 6 hours. However, 2-methynaphtho[1,2-d]oxazorium 3-butanesulfonate, which is an intended compound, was obtained in an amount of 3.3 g (a yield of 15%).

EXAMPLE 4

Synthesis of 2-methylphenanthro[1,2-d]thiazorium 3-butanesulfonate (a compound number 3.21 of the formula (3) above)

In a round bottom flask provided with a stirrer and a reflux condenser were placed 17.4 g (0.07 mole) of 2-methylphenanthro[1,2-d]thiazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 18.2 g of white crystals were obtained and the yield of the crystals (as the subject compound) was 70%.

EXAMPLE 5

Synthesis of 2-methyl-5-phenoxynaphtho[1,2-d]thiazorium 3-butanesulfonate (a compound number 3.23 of the formula (3) above)

In a round bottom flask provided with a stirrer and a reflux condenser were placed 20.4 g (0.07 mole) of 2-methyl-5-phenoxynaphtho[1,2-d]thiazole and 14 g (0.10 mole) of 1,4-butanesultone, and they were heated at 160° C. by dipping the flask in an oil bath. With stirring the contents, 28 ml (0.22 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 15.0 g of white crystals were obtained and the yield of the crystals (as the subject compound) was 50%.

EXAMPLE 6

Synthesis of 2-methyl-6-sulfonaphtho[1,2-d]thiazorium 3-butanesulfonate (a compound number 3 26 of the formula (3) above)

In a round bottom flask provided with a stirrer and a reflux condenser were placed 21.1 g (0.07 mole) of 2-methyl-6-sulfonaphtho[1,2-d]thiazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 19.3 g of white crystals were obtained and the yield of the crystals (as the subject compound) was 63%.

EXAMPLE 7

Synthesis of 2-methylnaphtho[1,2-d]selenazorium 3-butanesulfonate (a compound number 3.15 of the formula (3)

In a round bottom flask provided with a stirrer and a 2-methylnaphtho[1,2-d]selenazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 160° C. for hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 14.7 g of white crystals were obtained and the yield of the crystals (as the subject compound) was 55%.

EXAMPLE 8

Synthesis of 1,2-dimethylnaphtho[1,2-d]imidazorium 3-butanesulfonate (a compound number 3.37 of the formula (3) above)

In a round bottom flask provided with a stirrer and a reflux condenser were placed 13.7 g (0.07 mole) of 1,2-dimethylnaphtho[1,2-d]imidazole and 14 g (0.10 mole) of 1,4-butanesultone, and they were heated at 160° C. by dipping the flask in an oil bath. With stirring the contents, 28 ml (0.22 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 9.73 g of white crystals were obtained and the yield of the crystals (as the subject compound) was 42%.

EXAMPLE 9

Synthesis of 2-methylanthro[1,2-d]thiazorium 3-butanesulfonate (a compound number 3–58 of the formula (3) above)

In a round bottom flask provided with a stirrer and a reflux condenser were placed 17.4 g (0.07 mole) of 2-methylanthro[1,2-d]thiazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 160° C. for hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 15.6 g of white crystals were obtained and the yield of the crystals (as the subject compound) was 60%.

EXAMPLE 10

Synthesis of 2-methylthionaphtho[1,2-d]thiazorium 3-butanesulfonate (a compound number 3.60 of the formula (3) above)

In a round bottom flask provided with a stirrer and a reflux condenser were placed 16.2 g (0.07 mole) of 2-methylthionaphtho[1,2-d]thiazole and 14 g (0.10 mole) of 1,4-butanesultone, and they were heated at 160° C. by dipping the flask in an oil bath. With stirring the contents, 14 ml (0.11 mole) of boron trifluoride ethyl etherate was gradually added into the flask. The addition took 10 minutes. Then, the contents was caused to react keeping at 160° C. for 1 hour.

After the reaction was complete, the reaction mixture was cooled to a room temperature, and 280 ml of ethyl acetate was placed in the flask and mixed under stirring, whereby white crystals were deposited. The crystals were separated from the mixture by filtration and dried at 50° C. for 1 hour. Thus, 10.8 g of white crystals were obtained and the yield of the crystals (as the subject compound) was 58%.

I claim:

1. A process for preparing an alkyl sulfonate derivative comprising:

causing a nitrogen-containing heterocyclic compound represented by the following formula (1):

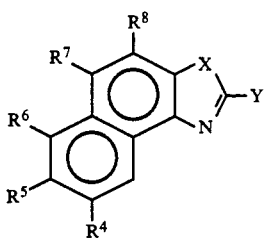

wherein X represents —O—, —S—, —NR$^1$—, —Se—, —Te— or —CR$^2$R$^3$—, in which each of R$^1$, R$^2$ and R$^3$ independently represents a hydrogen atom or a lower alkyl group which may be substituted with a halogen atom, a lower alkoxy group, an amino group or a hydroxy group and R$^2$ and R$^3$ may be bonded each other to form a 5 to 8-membered ring containing oxygen or nitrogen together with a carbon atom of a pyrrole ring to which R$^2$ and R$^3$ are bonded, Y represents a hydrogen atom, a mercapto group, an arylthio group which may be substituted with a halogen atom, an aralkyl group which may be substituted with a halogen atom, a sulfo group, a halogen atom, an alkyl group which may be substituted with a halogen atom, an alkylthio group which may be substituted with a sulfo group, an alkoxy group or an alkoxyalkoxy group, an alkylsulfonyloxy group which may be substituted with a halogen atom or an arylsulfonyloxy group which may be substituted with a halogen atom or an alkyl group and each of R$^4$, R$^5$, R$^6$, R$^7$ and R$^8$ independently represents a hydrogen atom, an alkyl group, an aryl group, an alkoxy group which may be substituted with a sulfo group, an aryloxy group, an alkylthio group, a haloalkyl group, a halogen atom, a cyano group, a carboxy group or a sulfo group;

to react in the presence of Lewis acid with an aliphatic sultone represented by the following formula (2):

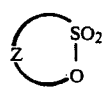

wherein Z represents an alkylene group which may substituted with an alkyl group, an alkoxy group or halogen atom;

to give an alkyl sulfonate derivative represented by the following formula (3):

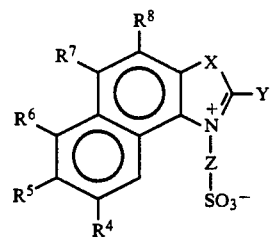

wherein Y, R$^4$, R$^5$, R$^6$, R$^7$, R$^8$, X and Z represent the meanings defined above.

2. The process for preparing an alkyl sulfonate derivative as claimed in claim 1, wherein said X represents —O—, —S—, —NR$^1$—, —Se— or —CR$^2$R$^3$—.

3. The process for preparing an alkyl sulfonate derivative as claimed in claim 1, wherein said Y represents a hydrogen atom, an alkyl group having 1 to 5 carbon atoms, an alkylthio group having 1 to 4 carbon atoms, a phenylthio group or a benzyl group.

4. The process for preparing an alkyl sulfonate derivative as claimed in claim 1, wherein each of R$^4$, R$^5$, R$^6$, R$^7$ and R$^8$ independently represents a hydrogen atom, an alkyl group having 1 to 3 carbon atoms, an aryl group having 6 to 14 carbon atoms, an alkoxy group having 1 to 25 carbon atoms which may be substituted with a sulfo group, a phenoxy group, an alkylthio group, a halogen atom, a cyano group, a carboxy group or a sulfo group.

5. The process for preparing an alkyl sulfonate derivative as claimed in claim 1, wherein said Z represents a linear alkylene group of 3 or 4 carbon atoms.

6. The process for preparing an alkyl sulfonate derivative as claimed in claim 1, wherein said Lewis acid is a boron trifluoride etherate.

7. A process for preparing an alkyl sulfonate derivative comprising:

causing a nitrogen-containing heterocyclic compound represented by the following formula (1):

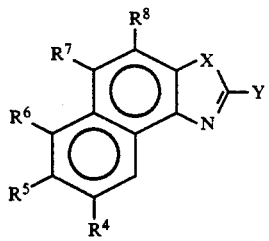

(1)

wherein X represents —O—, —S—, —NR¹—, —Se—, —Te— or —CR²R³—, in which each of R¹, R² and R³ independently represents a hydrogen atom or a lower alkyl group which may be substituted with a halogen atom, a lower alkoxy group, an amino group or a hydroxy group and R² and R³ may be bonded each other to form a 5 to 8-membered ring containing oxygen or nitrogen together with a carbon atom of a pyrrole ring to which R² and R³ are bonded, Y represents a hydrogen atom, a mercapto group, an arylthio group which may be substituted with a halogen atom, an aralkyl group which may be substituted with a halogen atom, a sulfo group, a halogen atom, an alkyl group which may be substituted with a halogen atom, an alkylthio group which may be substituted with a sulfo group, an alkoxy group or an alkoxyalkoxy group, an alkylsulfonyloxy group which may be substituted with a halogen atom or an arylsulfonyloxy group which may be substituted with a halogen atom or an alkyl group, R⁴ and R⁵, R⁵ and R⁶, R⁶ and R⁷ and R⁷ and R⁸ are, in at least one of the combinations, bonded each other to form an aromatic ring or a cycloalkene ring together with a divalent hydrocarbon group of a naphthalene ring to which R⁵, R⁶, R⁷ and R⁸ are bonded, and R⁴, R⁵, R⁶, R⁷ and R⁸ which do not participate the formation of the ring represent a hydrogen atom, an alkyl group, an aryl group, an alkoxy group which may be substituted with a sulfo group, an aryloxy group, an alkylthio group, a haloalkyl group, a halogen atom, a cyano group, a carboxy group or a sulfo group;

to react in the presence of Lewis acid with an aliphatic sultone represented by the following formula (2):

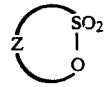

(2)

wherein Z represents an alkylene group which may substituted with an alkyl group, an alkoxy group or halogen atom;

to give an alkyl sulfonate derivative represented by the following formula (3):

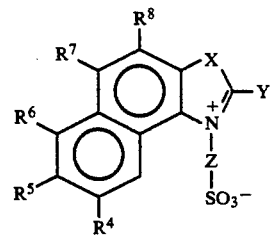

(3)

wherein Y, R⁴, R⁵, R⁶, R⁷, R⁸, X and Z represent the meanings defined above.

8. The process for preparing an alkyl sulfonate derivative as claimed in claim 7, wherein said X represents —O—, —S—, —NR¹—, —Se— or —CR²R³—.

9. The process for preparing an alkyl sulfonate derivative as claimed in claim 7, wherein said Y represents a hydrogen atom, an alkyl group having 1 to 5 carbon atoms, an alkylthio group having 1 to 4 carbon atoms, a phenylthio group or a benzyl group.

10. The process for preparing an alkyl sulfonate derivative as claimed in claim 7, wherein R⁴ and R⁵, R⁵ and R⁶, R⁶ and R⁷ or R⁷ and R⁸ are bonded each other to form a benzene ring or a cyclohexene with a divalent hydrocarbon group of a naphthalene ring.

11. The process for preparing an alkyl sulfonate derivative as claimed in claim 7, wherein said Z represents a linear alkylene group of 3 or 4 carbon atoms.

12. The process for preparing an alkyl sulfonate derivative as claimed in claim 7, wherein said Lewis acid is a boron trifluoride etherate.

* * * * *